(12) United States Patent
Ringlien (10) Patent No.: US 7,595,870 B2
(45) Date of Patent: Sep. 29, 2009

(54) OPTICAL INSPECTION OF CONTAINER WALLS

(75) Inventor: James A. Ringlien, Maumee, OH (US)

(73) Assignee: Owens-Brockway Glass Container Inc., Perrysburg, OH (US)

( * ) Notice: Subject to any disclaimer, the term of this patent is extended or adjusted under 35 U.S.C. 154(b) by 569 days.

(21) Appl. No.: 10/987,757

(22) Filed: Nov. 10, 2004

(65) Prior Publication Data

US 2006/0098191 A1 May 11, 2006

(51) Int. Cl.
*G01N 21/00* (2006.01)

(52) U.S. Cl. .................. 356/239.4; 356/239.6

(58) Field of Classification Search ............ None
See application file for complete search history.

(56) References Cited

U.S. PATENT DOCUMENTS

| | | | |
|---|---|---|---|
| 3,533,704 A | 10/1970 | Krenmayr | |
| 4,262,196 A | 4/1981 | Smith | |
| 4,280,624 A | 7/1981 | Ford | |
| 4,579,227 A | 4/1986 | Miller | |
| 4,606,634 A | 8/1986 | Bieringer | |
| 4,610,542 A | 9/1986 | Ringlien | |
| 4,644,151 A | 2/1987 | Juvinall | |
| 4,664,521 A * | 5/1987 | Scott et al. | 356/239.4 |
| 4,691,231 A | 9/1987 | Fitzmorris et al. | |
| 4,736,851 A | 4/1988 | Ricros et al. | |
| 4,931,632 A | 6/1990 | Brandt | |
| 4,945,228 A | 7/1990 | Juvinall et al. | |
| 4,948,956 A | 8/1990 | Fukuchi | |
| 5,004,909 A | 4/1991 | Fukuchi | |
| 5,059,031 A | 10/1991 | Hamel et al. | |
| 5,095,204 A | 3/1992 | Novini | |
| 5,229,837 A | 7/1993 | Osakada | |
| 5,233,186 A | 8/1993 | Ringlien | |
| 5,243,400 A | 9/1993 | Ringlien | |
| 5,444,237 A * | 8/1995 | Takizawa | 356/239.5 |
| 5,467,125 A * | 11/1995 | Yoshida | 348/127 |
| 6,239,869 B1 | 5/2001 | Heuft et al. | |
| 6,239,870 B1 | 5/2001 | Heuft | |
| 6,304,323 B1 | 10/2001 | Ishikura et al. | |
| 6,512,239 B1 | 1/2003 | Weiss et al. | |
| 6,621,573 B2 | 9/2003 | Shultz et al. | |
| 2006/0208172 A1* | 9/2006 | Akkerman et al. | 250/223 B |

FOREIGN PATENT DOCUMENTS

| | | |
|---|---|---|
| DE | 003611536 A1 | 10/1987 |
| EP | 0328374 A2 | 8/1989 |

(Continued)

*Primary Examiner*—Michael A Lyons
*Assistant Examiner*—Juan D Valentin (57) ABSTRACT

An apparatus for detecting blisters in a container wall includes a light source for directing light energy onto a container wall in such a way that portions of the light energy are reflected from surfaces of the container wall, including surfaces of blisters in the container wall. A light sensor is disposed to receive light energy reflected from the container wall, and an information processor is coupled to the sensor to detect a blister in the container wall as a bright image against a darker background. Light energy reflected from the inner and outer surfaces of the container wall preferably establish the darker background, and light energy reflected from surfaces of blisters within the container wall establish the bright image.

15 Claims, 5 Drawing Sheets

FOREIGN PATENT DOCUMENTS

| | | |
|---|---|---|
| GB | 2195178 | 3/1988 |
| JP | 358184537 A | 10/1983 |
| JP | 402103453 A | 4/1990 |
| JP | 08254505 | 10/1996 |
| WO | WO01/55705 | 8/2001 |

* cited by examiner

OPTICAL INSPECTION OF CONTAINER WALLS

The present invention is directed to inspection of containers for commercial variations that affect optical properties of the containers, and more particularly to an apparatus and method for detecting blisters and/or embossments in the sidewalls of glass containers.

BACKGROUND AND OBJECTS OF THE INVENTION

In the manufacture of containers such as glass bottles and jars, various types of anomalies can occur in the sidewalls, heels, bottoms, shoulders, necks and/or finishes of the containers. These anomalies, termed "commercial variations" in the art, can affect commercial acceptability of the containers. It has been proposed to employ electro-optical inspection techniques for detecting commercial variations that affect the optical properties of the containers. The basic principle is that a light source is positioned to direct light energy onto the container, and a light sensor is positioned to receive an image of a portion of the container illuminated by the light source. An information processor is coupled to the sensor to detect commercial variations in the container as a function of the light energy received at the sensor.

Blisters can be envisioned as air pockets in a container wall, which can arise for various reasons during the container manufacturing process. It has been proposed to detect blisters in container walls by transmitting light through the container walls and detecting the blisters as a function of refraction of the light at the edges of the blisters. See U.S. Pat. Nos. 5,233,186 and 5,243,400. However, this technique can be problematic for large flat blisters, in which the edges are relatively small. It is a general object of the present invention to provide an apparatus and method for enhanced detection of blisters and/or embossments in a container wall.

SUMMARY OF THE INVENTION

The present invention involves a number of aspects, which can be implemented separately from or more preferably in combination with each other.

An apparatus for detecting blisters in a container wall, in accordance with one aspect of a presently preferred embodiment of the invention, includes a light source for directing light energy onto a container wall in such a way that portions of the light energy are reflected from surfaces of the container wall, including surfaces of blisters in the container wall. A light sensor is disposed to receive light energy reflected from the container wall, and an information processor is coupled to the sensor to detect a blister in the container wall as a bright image against a darker background. Light energy reflected from the inner and outer surfaces of the container wall preferably establish the darker background, and light energy reflected from surfaces of blisters within the container wall establish the bright image. The container preferably is rotated around an axis, and the information processor preferably scans the light sensor at increments of container rotation. The light sensor preferably is a linear array light sensor having an axis parallel to the axis of rotation of the container, and the light source preferably is a diffuse light source. The linear array sensor preferably is disposed to receive light energy from a central portion of the diffuse light source reflected from interior and exterior surfaces of the container.

An apparatus for detecting embossments on a container wall, in accordance with another aspect of the presently preferred embodiment of the invention, includes a light source for directing light energy onto a container wall in such a way that portions of the light energy are reflected from surfaces of the container wall, including surfaces of embossments on the container wall. A light sensor is disposed to receive light energy reflected from the container wall, and an information processor is coupled to the sensor to detect an embossment on the container wall as a dark image against a brighter background. Light energy reflected from the inner and outer surfaces of the container wall preferably establish the brighter background, and light energy reflected from surfaces of embossments on the container wall establish the dark image.

An apparatus for detecting blisters and embossments in a container wall, in accordance with a further aspect of the presently preferred embodiment of the invention, includes a light source for directing light energy onto the container wall in such a way that a portion of the light energy is reflected from surfaces of the container wall, including surfaces of blisters in the container wall and surfaces of embossments on the container wall. A light sensor is disposed to receive light energy reflected from the container wall. An information processor is coupled to the light sensor to detect a blister as a bright image and an embossment as a dark image against an otherwise gray background of reflections from the container wall. In the preferred embodiment in accordance with this aspect of the invention, the gray background is established by light energy reflected from the inner and outer surfaces of the container wall.

BRIEF DESCRIPTION OF THE DRAWINGS

The invention, together with additional objects, features, advantages and aspects thereof, will best be understood from the following description, the appended claims and the accompanying drawings, in which:

DETAILED DESCRIPTION OF PREFERRED EMBODIMENTS

Figure 1:
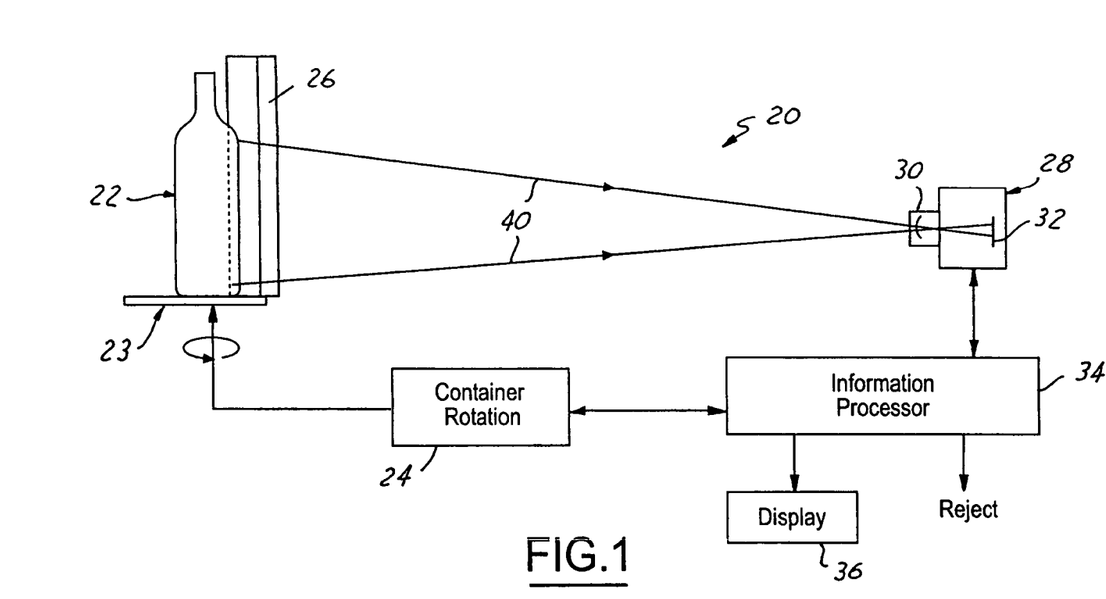
FIG. 1 is an electro-optical schematic diagram in side elevation that illustrates an apparatus for detecting blisters and/or embossments in a container sidewall in accordance with one presently preferred embodiment of the invention.
Figure 2:
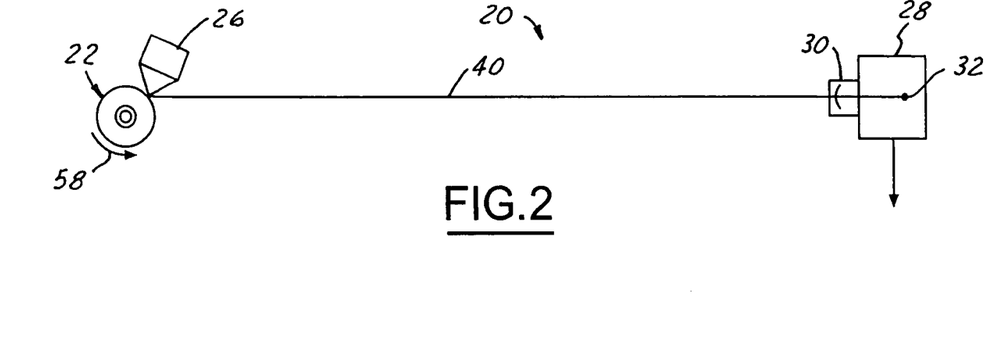
FIG. 2 is an electro-optical top plan schematic diagram of the optical portion of the apparatus in FIG. 1.
Figure 3:
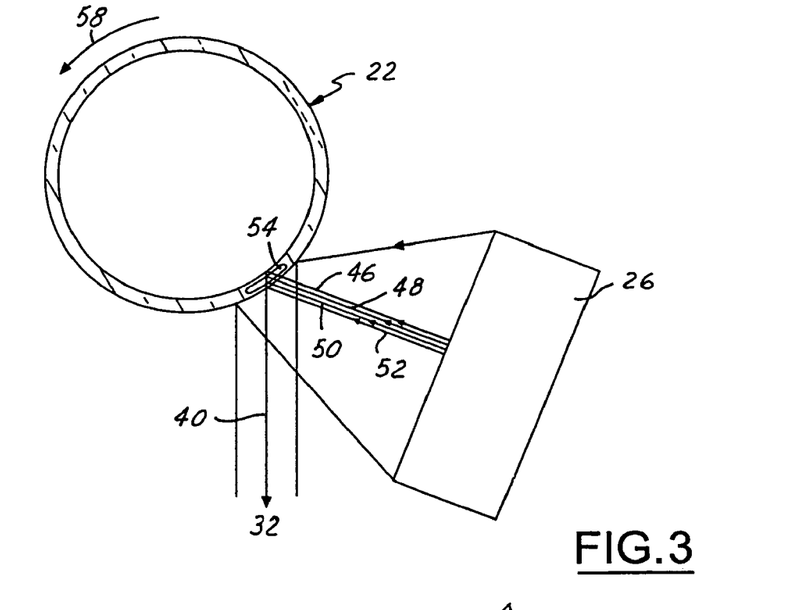
FIG. 3 is an enlargement of a portion of the apparatus as illustrated in FIG. 2.

FIGS. 1-3 illustrate an apparatus 20 for inspecting the sidewall of a container 22 in accordance with one presently preferred embodiment of the invention. Containers 22 preferably are brought to an inspection station, at which apparatus 20 is located, by means of a suitable conveyor 23 that presents the containers 22 in sequence for inspection. Suitable conveyors are disclosed in U.S. Pat. Nos. 4,378,493 and 6,581, 751. Containers are presented in sequence for inspection, and are coupled to a suitable device 24 for rotating each container 22 around an axis of rotation, which preferably is coincident with the central axis of the container. Suitable drive roller devices 24 are disclosed in the U.S. Patents noted immediately above. A diffuse light source 26 is positioned to direct light energy onto the exterior surface of container 22. Light energy reflected from the surfaces on and within the container sidewall is received at a camera 28. Camera 28 includes an entrance lens system 30, through which the reflected light energy is directed through an entrance pupil onto a light sensor 32. Light sensor 32 preferably comprises a linear array light sensor having a long dimension or axis parallel to the axis of rotation of container 22. Thus, the axis or long dimension of linear array sensor 32 extends from top to bottom in FIG. 1, and into the page in FIG. 2. An area array sensor could be used in place of a linear array sensor, from which a selected column of sensor elements would be employed for detection of blisters and/or embossments.

An information processor 34 is coupled to camera 32 for scanning information from sensor 32. Information processor 34 is also coupled to container rotation device 24 for controlling rotation of container 22 at the inspection station, and for scanning sensor 32 at increments of container rotation. Such increments of container rotation may comprise equal angular increments of container rotation, or equal time increments during which container 22 is rotated at constant velocity. Information processor 34 is coupled to a display 36 for displaying inspection data to an operator (FIGS. 7A-7C and 9), and to a suitable reject mechanism for removing containers 22 that do not pass inspection.

FIG. 3 illustrates interaction between diffuse light source 26 and container 22 in greater detail. Light energy from source 26 is incident on the outer surface of container 22 over an angular portion of the container surface, and at an angle such that a bundle of light rays is reflected from surfaces of the container sidewall, including the surfaces of blisters within and embossments on the container sidewall. A chief reflection ray 40 is illustrated in FIG. 3 (and FIGS. 1-2). The term "chief ray" has its usual meaning in the art, and refers to the ray directed toward the center of the entrance pupil of lens 30 at camera 28 (FIGS. 1 and 2). It will be understood that each chief ray 40 is surrounded by a cone of rays that will be accepted through the entrance pupil of the camera lens and focused onto light sensor 32. However, the present invention is illustrated in the drawings and discussed hereinafter in connection with the chief reflection rays for purposes of simplification. It will be noted in FIG. 3 that the chief ray 40 preferably is generated by reflections of light energy emanating from the central portion of diffuse light source 26.

Figure 4:
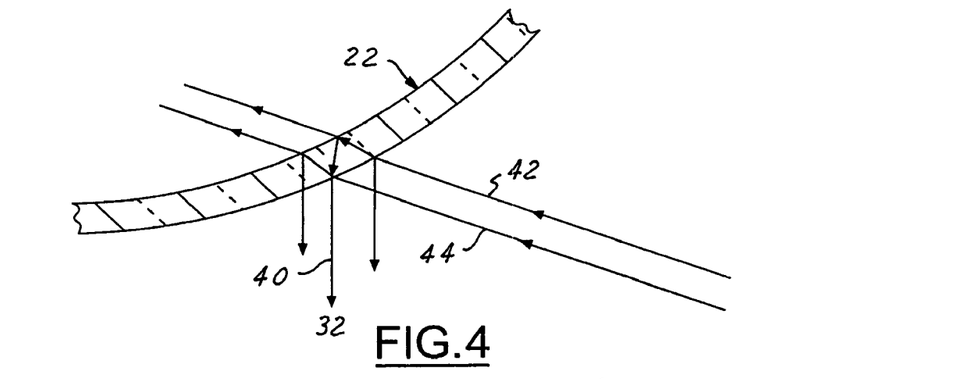
FIGS. 4, 5 and 6A to 6C are fragmentary schematic illustrations of portions of FIG. 3 for explaining operation of the invention.

FIG. 4 illustrates reflections of light energy from a container sidewall without blisters or embossments. Each ray 42, 44 from light source 26 is incident on the outer surface of the container sidewall, and is partially reflected from and partially refracted into the container sidewall. The light energy that enters the container sidewall is incident on the inside surface of the sidewall, and is partially reflected from and partially refracted through the inside surface. In the specific situation illustrated in FIG. 4, the portion of ray 42 reflected from the inside surface of the container sidewall is refracted at and emerges from the outside surface of the container sidewall at the point of incidence of ray 44 onto the outside surface of the container sidewall. Thus, reflected chief ray path 40 directed toward sensor 32 includes the portion of ray 44 reflected from the outer surface of the container sidewall, and the portion of ray 42 refracted into the container sidewall, reflected from the inside surface of the container sidewall, and refracted at the outside surface of the container sidewall. (Not all reflections and refractions are shown in FIG. 4, or in FIGS. 5-6C, for purposes of simplicity.)

Figure 5:
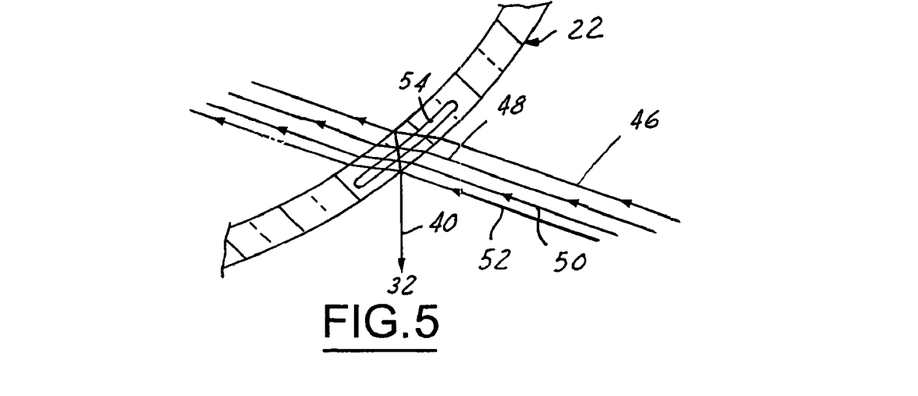

FIG. 5 illustrates refractions and reflections for detecting a blister 54 within the container sidewall. Four rays 46-52 are shown incident on the container sidewall from light source 26. Blister 54 has air/glass surfaces at which reflections and refractions occur. As in FIG. 4, a portion of each light ray will be reflected from each surface of the blister and a portion (depending upon the angle of incidence and the index of refraction of the glass) will be refracted at each surface of the blister. A portion of light ray 46 illustrated in FIG. 5 is refracted at the outer surface of the container sidewall, refracted again at the outer surface of blister 54, refracted a third time at the inner surface of blister 54 and then reflected from the inside surface of the container sidewall. This reflected portion of light ray 46 is again refracted at the inner surface of blister 54, at the outer surface of blister 54 and at the outer surface of the sidewall to form a portion of light ray 40 directed toward sensor 32. The portion of light ray 48 that forms part of ray 40 is refracted at the outer surface of the container sidewall and at the outer surface of blister 54, reflected from the inner surface of blister 54, refracted at the outer surface of blister 54 and at the outer surface of the container sidewall, and emerges from the container sidewall. Likewise, the portion of ray 50 that forms part of ray 40 is refracted at the outer surface of the container sidewall, reflected from the outer surface of blister 54 and refracted at the outer surface of the container sidewall. The portion of ray 52 that forms part of ray 40 is reflected at the outer surface of the container sidewall. (Directional words such as "inner," "outer," "inside" and "outside" are employed by way of description and not limitation with respect to the axis of container 22. Directional words such as "upper" and "lower" are employed by way of description and not limitation with respect to the upright orientation of the container illustrated in FIG. 1.) Thus, the presence of blister 54 (FIG. 5) in the container sidewall, as compared with the absence of such a blister (FIG. 4), means that additional light energy will be reflected from the container sidewall as part of chief ray 40 directed to the sensor. Thus, as a general proposition, the presence of a blister 54 in the container sidewall increases the amount of energy directed onto the sensor.

Figure 6A:
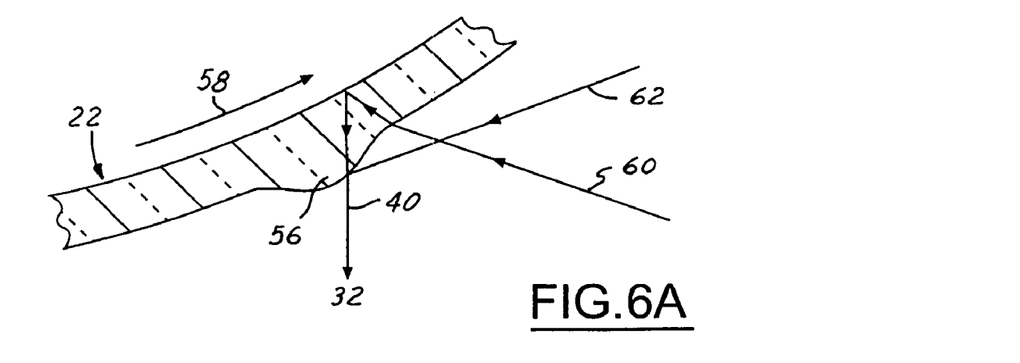
Figure 6B:
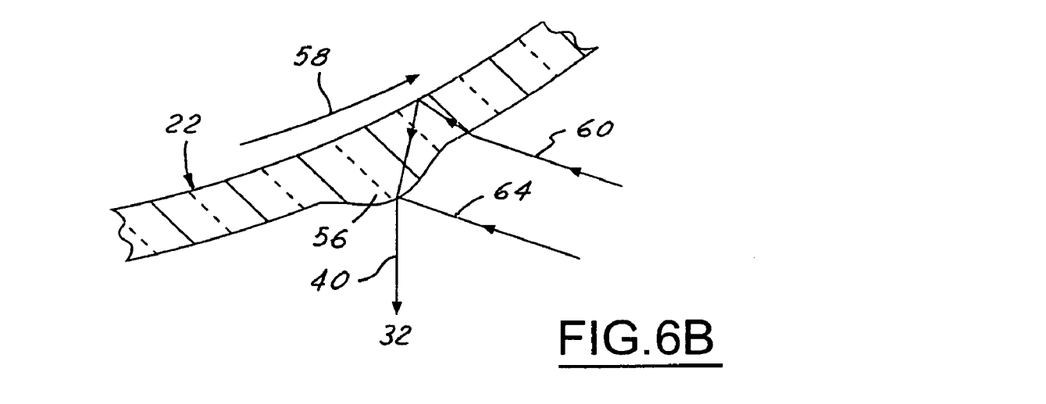
Figure 6C:
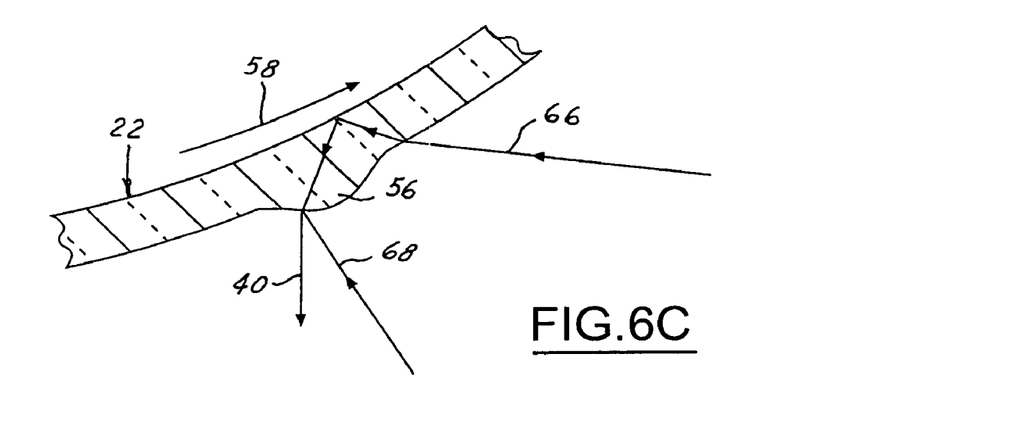

FIGS. 6A-6C illustrate operation in connection with an embossment 56 on the outside surface of the container sidewall. FIGS. 6A-6C show reflections along the path of chief ray 40 from three different points on an embossed surface feature 56 as the bottle rotates slightly in the direction 58 between views 6A and 6B, and again between the views of FIGS. 6B and 6C. Whether the sensor 32 (FIGS. 1 and 2) receives one or more reflected rays depends upon where on the embossed feature the light sensor is focused and upon the angular extent or size of the light source. For example, in the container position of FIG. 6A, chief reflection ray 40 would include a portion of incident ray 60, but not ray 62 unless the diffuse light source 26 (FIGS. 1-3) is very wide. In FIG. 6B, chief ray 40 directed to sensor 32 would include a portion of ray 60 and a portion of ray 64 reflected from the outside surface of the embossment 56. In FIG. 6C, the chief reflected ray 40 would include a portion of ray 66, but would only include a portion of ray 68 if the diffuse light source were very wide. Thus, as a general proposition, the presence of an embossment 56 on the surface of the container 22 tends to diffuse or scatter the incident light energy from the light source. Light energy directed onto the sensor typically is either the same as or less than the light energy directed onto the sensor in the absence of an embossment or a blister (FIG. 4).

Thus, as a general proposition, the presence of a blister in the container sidewall increases the amount of light energy directed onto a sensor 32, whereas the presence of an embossment on the surface of the container sidewall reduces the amount of light energy directed onto the sensor. This is graphically illustrated in FIGS. 7A-7D and 9. It will be appreciated that FIGS. 4-6C illustrate operation in only one plane and in association with only one reflected chief ray 40. There will be an infinite number of chief rays 40 within the vertical field of view (FIG. 1) of sensor 32.

Figure 7A:
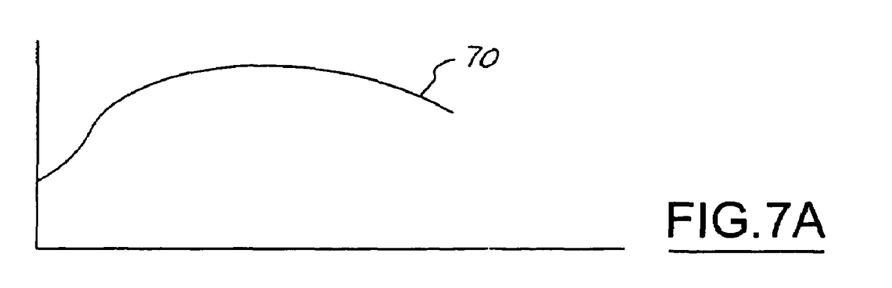
FIGS. 7A-7D are graphic illustrations useful for explaining operation of the invention.
Figure 7B:
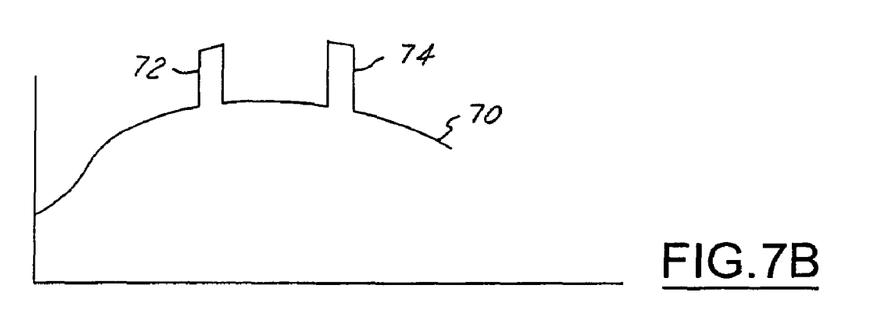
Figure 7C:
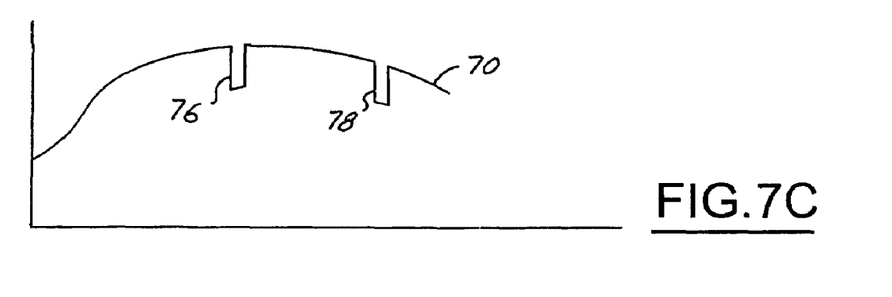
Figure 7D:
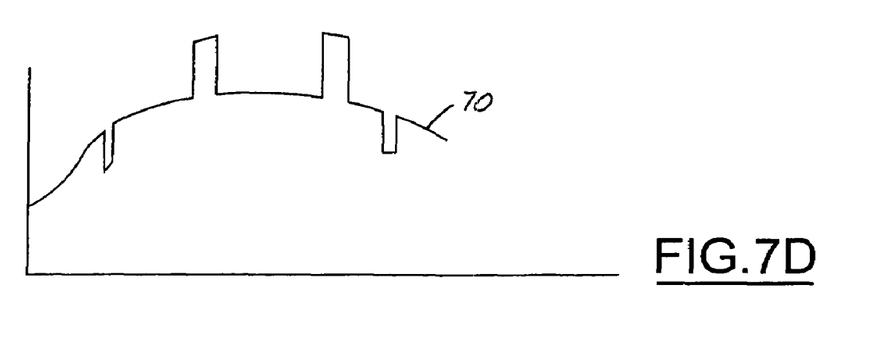

FIGS. 7A-7D are each a graphic illustration of reflected light intensity versus axial position along a container for one scan along the container and at a particular angular position of the container. In each illustration, the ordinate indicates light intensity while the abscissa indicates vertical axial position on the container. FIG. 7A illustrates the results of scanning a container at an angular position having no blisters or embossments. Light intensity 70 at sensor 32 is generally uniform as a function of vertical axial position on the container. FIG. 7B illustrates the additive effect of reflections 72, 74 from blisters in the container sidewall. In other words, reflections 72, 74 are superimposed on the generally uniform light energy 70 of FIG. 7A. FIG. 7C illustrates the subtractive effect of embossments on the container surface, with reductions 76, 78 due to embossments as compared with the generally uniform level 70 of FIG. 7A. FIG. 7D illustrates the cumulative effect of both blisters and embossments in the container sidewall.

Figure 8:
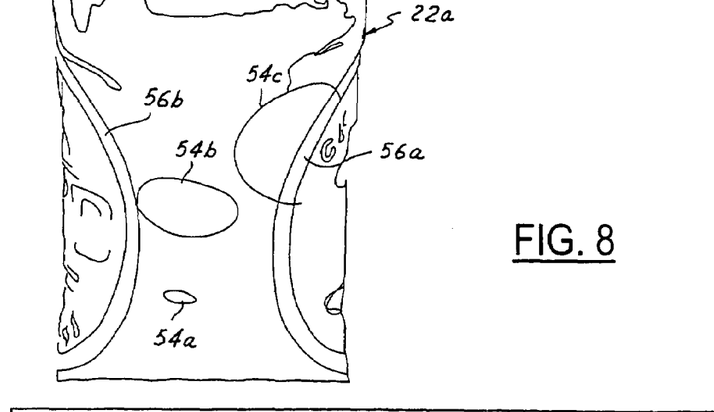
FIG. 8 is a fragmentary side elevational view of an exemplary container wall that can be inspected in accordance with the present invention.

FIG. 8 is a fragmentary elevational view of a container 22a having sidewall blisters 54a, 54b and 54c, and surface embossments 56a, 56b in the form of decorations or logos molded into the container sidewall.

Figure 9:
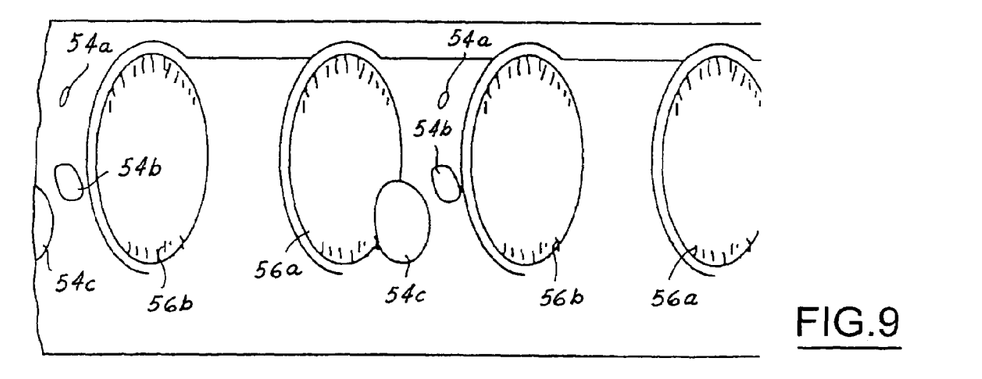
FIG. 9 is a fragmentary view of a display of blisters and embossments on the container sidewall of FIG. 8 as detected by the apparatus of FIGS. 1-3.

FIG. 9 is a graphic illustration of a display at 36 in FIG. 1 from inspecting the container of FIG. 8. The graphic illustration of FIG. 9 depicts two full rotations of container 22a (FIG. 8). In the display of FIG. 9, which depicts nearly two full revolutions, and with the intensity level 70 (FIGS. 7A-7D) having no blisters or bubbles establishing a mid level or gray intensity background, blisters 54a,54b,54c appear as bright images against the gray background due to the additive reflection effect of the blisters previously discussed, while embossments 56a, 56b appear as dark images against the gray background due to the subtractive reflective effect of embossments previously discussed.

Figure 10:
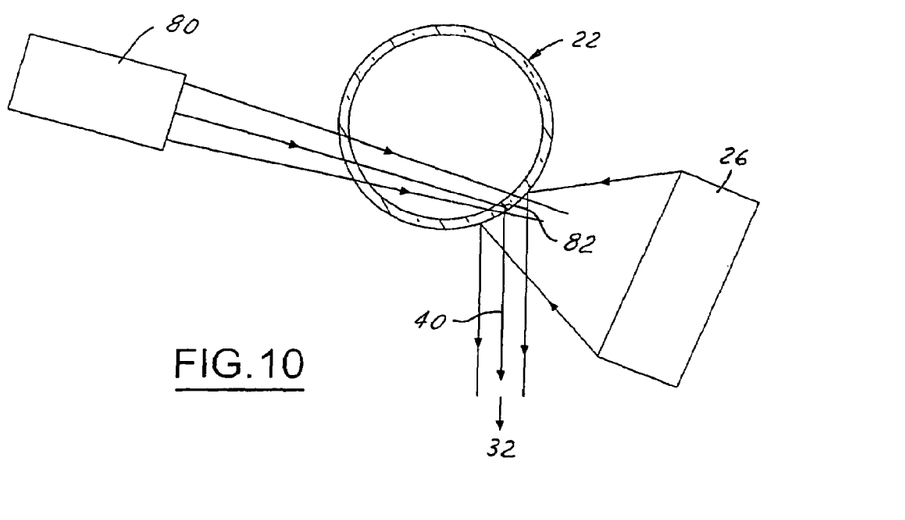
FIG. 10 is a fragmentary electro-optical schematic diagram of a modification to the embodiment of FIGS. 1-3.

FIG. 10 illustrates a modification to the embodiment of FIGS. 1-3, in which a vertical check detection light source 80 is positioned to direct light energy through the container sidewall onto the portion of the container illuminated by light source 26 from interiorly of the container. A vertical check 82 in the container sidewall, which is a minute vertically oriented crack in the container sidewall, functions as a mirror and reflects light energy along the path of chief ray 40. Check detection light source 80 may be as disclosed in U.S. Pat. No. 4,584,469 or 5,637,864. Information processor 34 (FIG. 1) can readily distinguish between vertical checks in the container sidewall and blisters in the container sidewall by the angular dimension of the reflection. In other words, in the unwrapped image of the container sidewall (FIG. 9), a vertical check will have a relatively small horizontal (container rotation) dimension as compared with a blister.

There thus have been disclosed a method and apparatus that fully satisfy all of the objects and aims previously set forth. The invention has been disclosed in conjunction with two presently preferred embodiments thereof, and a number of modifications and variations have been discussed. Other modifications and variations readily will suggest themselves to persons of ordinary skill in the art. The invention is intended to embrace all such modifications and variations as fall within the spirit and broad scope of the appended claims.

The invention claimed is:

1. Apparatus for detecting blisters in a container wall having an inner surface and an outer surface, which includes:
    a light source for directing light energy onto a container wall in such a way that portions of the light energy are reflected from surfaces of the container wall, including surfaces of blisters in the container wall,
    a light sensor disposed to receive light energy reflected from the container wall, and
    an information processor coupled to said light sensor to detect a blister in the container wall as a bright image against a darker background,
    said light sensor being disposed to receive light energy reflected from inner and outer surfaces of the container wall to establish said darker background at said sensor, and to receive light energy reflected from surfaces of blisters within the container wall establish said bright image.

2. The apparatus set forth in claim 1 in which said light sensor is disposed to receive light energy from said source reflected from surfaces of embossments on the container wall, and in which said information processor is coupled to said sensor to detect a blister as a bright image and an embossment as a dark image against a gray background established at said sensor by reflections from said inner and outer surfaces onto said sensor.

3. The apparatus set forth in claim 1 including means for rotating the container around an axis, said information processor scanning said light sensor at increments of container rotation.

4. The apparatus set forth in claim 3 wherein said light source is a diffuse light source, and said light sensor is a linear array light sensor having an axis parallel to said axis of rotation of the container.

5. The apparatus set forth in claim 4 wherein said linear array light sensor is disposed to receive light energy from a central portion of said diffuse light source reflected from interior and exterior surfaces of the container.

6. Apparatus for detecting embossments on a container wall having an inner surface and outer surface, which includes:
    a light source for directing light energy onto a container wall in such a way that portions of the light energy are reflected from surfaces of the container wall, including surfaces of embossments on the container wall,
    a light sensor disposed to receive light energy reflected from the container wall, and
    an information processor coupled to said light sensor to detect an embossment on the container wall as a dark image against a brighter background,
    said light sensor being disposed to receive light energy reflected from inner and outer surfaces of the container wall to establish said brighter background at said sensor, and to receive light energy reflected from surfaces of embossments to establish said dark image at said sensor.

7. The apparatus set forth in claim 6 in which said light sensor is disposed to receive light energy from said source reflected from surfaces of blisters in the container wall, and in which said information processor is coupled to said sensor to detect a blister as a bright image and an embossment as a dark image against a gray background established at said sensor by reflections from said inner and outer surfaces onto said sensor.

8. The apparatus set forth in claim 6 including means for rotating the container around an axis, said information processor scanning said light sensor at increments of container rotation.

9. The apparatus set forth in claim 8 wherein said light source is a diffuse light source, and said light sensor is a linear array light sensor having an axis parallel to said axis of rotation of the container.

10. The apparatus set forth in claim 9 wherein said linear array light sensor is disposed to receive light energy from a central portion of said diffuse light source reflected from interior and exterior surfaces of the container.

11. Apparatus for detecting blisters in and embossments on a container wall having an inner surface and an outer surface, which includes:
- a light source for directing light energy onto a container wall in such a way that portions of the light energy are reflected from surfaces of the container wall, including surfaces of blisters in the container wall and surfaces of embossments on the container wall,
- a light sensor disposed to receive light energy reflected from the container wall, and
- an information processor coupled to said light sensor,
- said light sensor being disposed to receive light energy reflected from inner and outer surfaces of the container wall to establish a gray background at said sensor, to receive light energy reflected from surfaces of blisters within the container wall to establish bright images at said sensor, and to receive light energy reflected from embossments on the container wall to establish dark images at said sensor,
- said information processor being adapted to detect blisters in and embossments on the container wall as bright and dark images, respectively, against said gray background.

12. The apparatus set forth in claim 11 including means for rotating the container around an axis, said information processor scanning said light sensor at increments of container rotation.

13. The apparatus set forth in claim 12 wherein said light source is a diffuse light source, and said light sensor is a linear array light sensor having an axis parallel to said axis of rotation of the container.

14. The apparatus set forth in claim 13 wherein said linear array light sensor is disposed to receive light energy from a central portion of said diffuse light source reflected from inner and outer surfaces of the container wall.

15. A method of detecting blisters in and embossments on a container wall having inner and outer surfaces, which includes the steps of:
- (a) directing light energy onto a container wall in such a way that portions of the light energy are reflected from surfaces of the container wall, including surfaces of blisters in and embossments on the container wall,
- (b) receiving at a light sensor light energy reflected from the container wall, including light energy reflected from inner and outer surfaces of the container wall to establish a gray background at said sensor, light energy reflected from blisters in the container wall to establish bright images at said sensor, and light energy reflected from embossments on the container wall to establish dark images at said sensor, and
- (c) detecting blisters in and embossments on the container wall as respective bright and dark images at said sensor against said gray background.

* * * * *